(12) United States Patent
Hsu et al.

(10) Patent No.: US 8,271,262 B1
(45) Date of Patent: Sep. 18, 2012

(54) PORTABLE LIP READING SENSOR SYSTEM

(75) Inventors: Ying Hsu, Irvine, CA (US); Virgilio Villacorta, Corona, CA (US); W. Eric Boyd, San Clemente, CA (US)

(73) Assignee: ISC8 Inc., Costa Mesa, CA (US)

( * ) Notice: Subject to any disclaimer, the term of this patent is extended or adjusted under 35 U.S.C. 154(b) by 556 days.

(21) Appl. No.: 12/586,477

(22) Filed: Sep. 22, 2009

Related U.S. Application Data

(60) Provisional application No. 61/192,727, filed on Sep. 22, 2008.

(51) Int. Cl.
| | | |
|---|---|---|
| G10L 15/24 | (2006.01) | |
| G10L 21/00 | (2006.01) | |
| G10L 11/02 | (2006.01) | |
| G06F 17/28 | (2006.01) | |
| G10L 11/04 | (2006.01) | |
| G10L 13/00 | (2006.01) | |

(52) U.S. Cl. ............. 704/3; 704/206; 704/251; 704/260
(58) Field of Classification Search ................ 704/1–10, 704/200, 206, 251–255, 260, 500–504, E17.001–E17.016, 704/E15.001–E15.05, E11.001–E11.006; 382/100, 114–118, 128–133, 181, 325; 379/52
See application file for complete search history.

(56) References Cited

U.S. PATENT DOCUMENTS

| | | | | | |
|---|---|---|---|---|---|
| 4,757,541 | A | * | 7/1988 | Beadles ........................ | 704/254 |
| 4,975,960 | A | * | 12/1990 | Petajan ........................ | 704/251 |
| 5,473,726 | A | * | 12/1995 | Marshall ...................... | 704/231 |
| 5,774,591 | A | * | 6/1998 | Black et al. .................. | 382/236 |
| 5,806,036 | A | * | 9/1998 | Stork ........................... | 704/260 |
| 5,818,359 | A | * | 10/1998 | Beach .............................. | 341/21 |
| 5,933,527 | A | * | 8/1999 | Ishikawa ...................... | 382/190 |
| 6,115,482 | A | * | 9/2000 | Sears et al. .................... | 382/114 |
| 6,354,748 | B1 | * | 3/2002 | Vrvilo ........................... | 709/204 |
| 7,015,954 | B1 | * | 3/2006 | Foote et al. ................ | 348/218.1 |
| 7,082,393 | B2 | * | 7/2006 | Lahr ............................. | 704/233 |
| 8,199,006 | B2 | * | 6/2012 | Liu et al. ..................... | 340/540 |
| 2002/0194005 | A1 | * | 12/2002 | Lahr ............................ | 704/271 |
| 2003/0103873 | A1 | * | 6/2003 | Greschitz et al. .......... | 422/82.01 |
| 2004/0071395 | A1 | * | 4/2004 | Hsu et al. ........................ | 385/22 |
| 2006/0193494 | A1 | * | 8/2006 | Toyama ....................... | 382/103 |
| 2007/0195160 | A1 | * | 8/2007 | Koselka et al. ................ | 348/42 |
| 2008/0100572 | A1 | * | 5/2008 | Boillot .......................... | 345/158 |
| 2008/0154613 | A1 | * | 6/2008 | Haulick et al. ............... | 704/275 |
| 2009/0140863 | A1 | * | 6/2009 | Liu et al. ................... | 340/573.1 |
| 2009/0174658 | A1 | * | 7/2009 | Blatchley et al. ............ | 345/158 |

OTHER PUBLICATIONS

Harrison, Reid R and Christof Koch. "A Robust Analog VLSI Reichardt Motion Sensor." Analog Integrated Circuits and Signal Processing, vol. 24, pp. 213-229. Feb. 14, 2000. Kluwer Academic Publishers.*

* cited by examiner

*Primary Examiner* — Pierre-Louis Desir
*Assistant Examiner* — David Kovacek
(74) *Attorney, Agent, or Firm* — W. Eric Boyd, Esq.

(57) ABSTRACT

The invention comprises a lip reading device having a capacitive array for enhanced portable speech recognition.
The capacitive array of the invention produces a sequence of signal frames or signal data sets (i.e., digitized output) representative of the proximity and motion of a user's lips at a predetermined sample rate and resolution.
The sequence of signal data sets is stored in a first electronic memory and are compared against a reference data set representative of a predetermined acoustic signal stored in a second electronic memory.
The attributes of signal data set are compared against the reference data set for likely data matches based on predetermined criteria.

6 Claims, 1 Drawing Sheet

PORTABLE LIP READING SENSOR SYSTEM

CROSS-REFERENCE TO RELATED APPLICATIONS

This application claims the benefit of U.S. Provisional Patent Application No. 61/192,727, filed on Sep. 22, 2008 entitled "Portable Lip Reader" pursuant to 35 USC 119, which application is incorporated fully herein by reference.

STATEMENT REGARDING FEDERALLY SPONSORED RESEARCH AND DEVELOPMENT

N/A

FIELD OF THE INVENTION

The invention relates generally to the field of lip reader and acoustic enhancement systems.

More specifically, the invention relates to a portable lip reading sensor system having a capacitive sensing array to measure lip movements of a user during speech.

BACKGROUND OF THE INVENTION

While speech recognition has advanced significantly over the past decade, one major problem that continues to plague this technology is performance in acoustically noisy environments. Various methods for noise reduction to enhance acoustic speech signatures have been developed for speech recognition such as the use of multiple loudspeakers or the use of video inputs. Unfortunately, background noise consisting of multiple acoustic sources can confound these enhancements—the so-called cocktail room effect.

One method of increasing the signal-to-noise ratio of the intended speaker is the use of multiple microphones, that is, beam forming microphone technology. Such applications have already found their way into the marketplace with demonstrated performance improvement in speech recognition. Unfortunately these devices typically require some minimum spacing between microphones that constrains miniaturization. For instance, prior art devices are currently over 10 cm at their longest dimension.

Another approach to the enhancement of speech recognition in acoustically noisy environments is the use of non-acoustic inputs. Video enhancement of audio speech recognition algorithms—that is, the use of a camera to monitor the movement of the lip region or facial movements—has been explored by a number of leading research corporations, including Intel Corporation and Microsoft Corporation. Making use of visual and/or near-infrared cameras in speech recognition technology developed by these corporations has shown an increase in performance in very noisy environments.

The use of video inputs for speech recognition undesirably runs into the problem of poor performance in changing or poor lighting—e.g., susceptibility to low contrast environments. Moreover, the use of cameras (especially one that would be constantly running) is problematic for portable devices which require a low power solution.

Even more exotic methods of enhancing speech recognition have been developed to make use of electromyographic information—that is, the direct measurement of the motor neurons involved in speech. However, because of the exotic nature of the recording methods, such technologies are difficult to implement in widespread professional or consumer intended markets.

What is needed is a device that is relatively inexpensive, can be implemented in a small device, is low power and which permits enhanced and reliable speech recognition in acoustically noisy environments.

SUMMARY OF THE INVENTION

The invention comprises a lip reading device having a capacitive array with an output representative of the movement of a user's lips or facial features for enhanced portable speech recognition.

The output of the capacitive array of the invention is processed by first electronic circuitry, the output of which comprises a sequence of signal frames or signal data sets (i.e., digitized output of the capacitive array) representative of the proximity and motion of a user's lips at a predetermined sample rate and resolution.

The sequence of signal data sets is stored in a first electronic memory and is compared against a reference data set representative of a predetermined acoustic signal stored in a second electronic memory. Predetermined attributes of the selected signal data set are compared against the reference data set for likely data matches based on user-selected criteria.

The device may be utilized in an additional mode—i.e. in addition to acoustics—to enhance the recognition of spoken input from a user of a portable communication device.

The non-acoustic mode of input to a speech recognition algorithm of the invention is a feature that permits enhanced performance in acoustically noisy environments.

Additionally, a user can optionally use the device to introduce a multi-modal speech signature detection system (i.e., biometric) for security locking/unlocking of portable devices. This technology may desirably be incorporated in the growing market of "smart phones"-portable communication devices that have the computational processing power to run a multi-modal speech recognition algorithm.

The disclosed portable lip reading device may further be used for enhancing overall performance of language translation, voice command and voice navigation on devices such as a portable communication device.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE INVENTION

Figure 1:
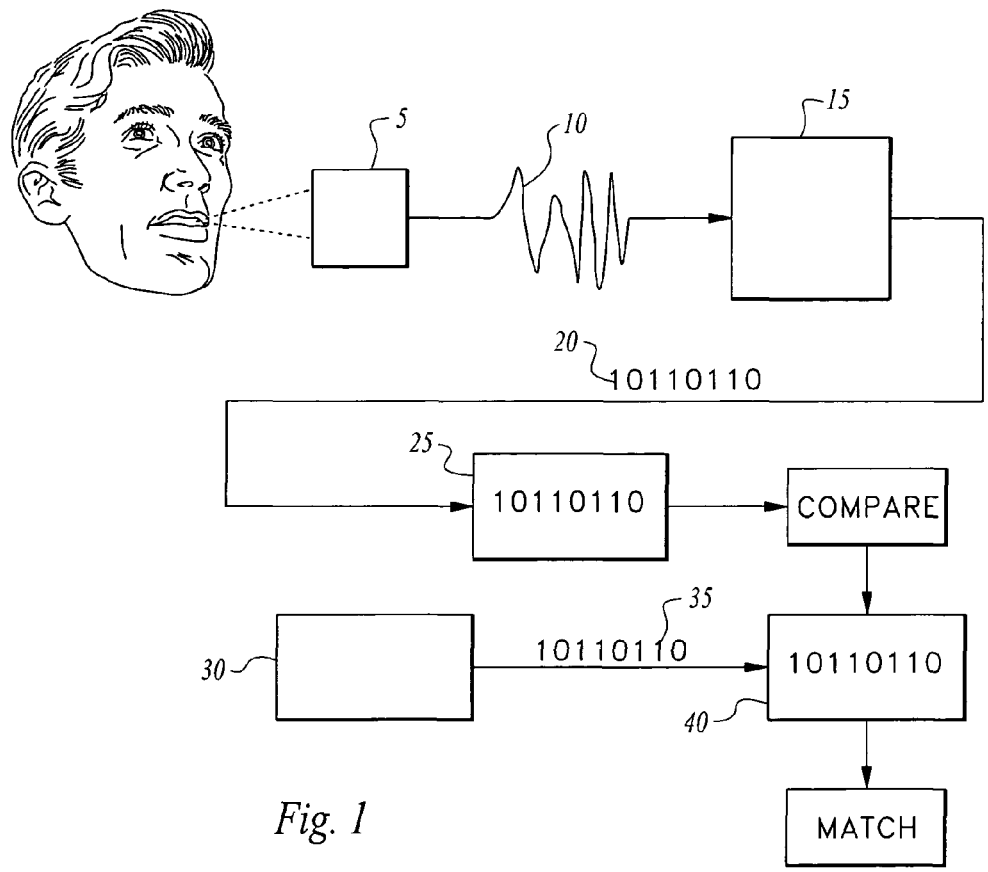
FIG. 1 is a block operational diagram of a preferred embodiment of the invention.

Turning now to the figures wherein like numerals designate like elements among the several views, a preferred embodiment of an operational block diagram of the invention is illustrated in FIG. 1.

The invention generally comprises a capacitive array 5 having an array output 10 representative of the movement of a user's lips or facial features, first electronic circuitry 15 for the receiving and processing (i.e., digitizing such as by an analog to digital converter) of the array output 10 into one or more signal data sets 20, a first electronic memory 25 for the receiving and storing of the one or more signal data sets 20, a second electronic memory 30 for storing one or more predefined reference data sets 35 representative of a predetermined set of acoustic signals and second electronic circuitry 40 for comparing at least one of the signal data sets 20 with at least one reference data set 35.

A key innovation of the instant invention is the use of a capacitive (lip position sensing) array 5 utilized to measure lip or facial movements of the user when the invention is held proximal the user's face. Capacitive array 5 is desirably relatively small, generally approximating the dimensions of the human lips (e.g. about six cm by about four cm).

Figure 2:
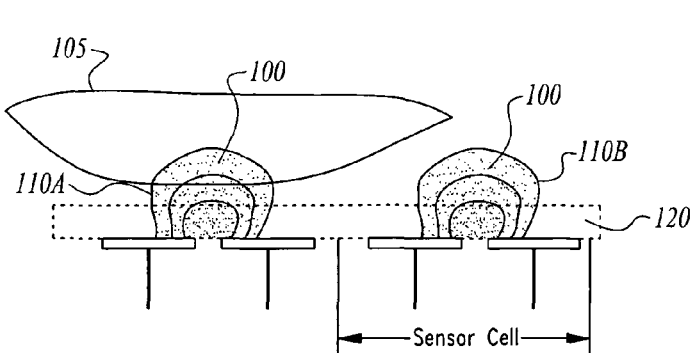
FIG. 2 is a cross-section of the capacitive array of the invention.

As seen in FIG. 2, a preferred embodiment of capacitive array 5 comprises one or more capacitive sensing array pairs for the non-contact measurement of the lip profile or movement of the user when the device is held proximal the user's face.

As shown in FIG. 2, each sensor cell measures the capacitance between two neighboring capacitive plates. Feedback capacitance 100 is inhibited by the proximity of the lips 105 brought near the capacitive plates (see 110A), while feedback capacitance 100 is maximal when the lip surface is far from the sensor surface (see 110B).

Protective layer 120 represents a protective coating to protect the sensor surface from environmental damage.

Capacitive array 5 of the invention produces one or a sequence of signal frames or signal data sets (i.e., digitized signals) using first electronic circuitry 15, the output of which is representative of the proximity and location/movement of a user's lips generated at a predetermined sample/frame rate and resolution.

The sequence of signal data sets 20 is stored in a first electronic memory 25 and are compared against one or more reference data sets 35 representative of one or more predetermined acoustic signals stored in a second electronic memory 30. The signal data set/reference data set comparison operation is desirably performed by an algorithm implemented in suitable electronic circuitry.

As stated, the attributes of one or more signal data sets 20 are compared against one or more reference data sets 35 for characteristics based on predetermined criteria. If the predetermined attributes are identified in the signal data set during the comparison operation, a match is detected and is flagged and an output generated for subsequent use by the device.

Sensor arrays similar to those discussed above have been successfully utilized in low-power devices to allow biometric measurement of fingerprints for portable devices and are a lower power alternative to the use of video cameras in similar speech enhancement applications.

Measurement of differences in capacitance using such a capacitive array desirably minimize potential measurement errors due to environmental influences (e.g. temperature and humidity). Moreover, measurements made by such a capacitive array are invariant to contrast/lighting conditions as the measurement depends only on distance of skin or lips to the array.

In order to approximate the higher performance of a video-based speech enhancement device, a preferred embodiment of the lip-reading sensor of the invention would desirably comprise:

1. A 640×480 array of sensors over a six by four cm surface,
2. Equivalent signal data frame rate of 10 frames per second or better,
3. Capacitive sensitivity to measure lip movements when the sensor array is a distance of about two to four cm from the user's lips.

As discussed, the disclosed device has a potentially large application community as it may be used for enhanced voice navigation of portable multi-media communication devices (smart phones). This is especially true if the sensor surface is integrated behind the display surface. If used in conjunction with speech/language translation or speech-to-text technology, the sensor invention may be used to also enhance communication in noisy environments by sending a computerized voice to a receiving handset.

Figure 3:
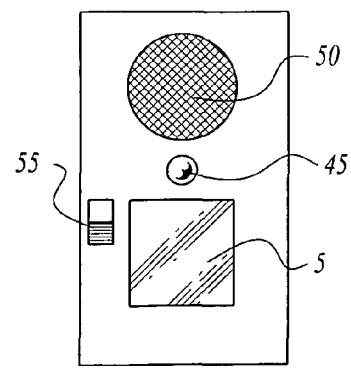
FIG. 3 shows a preferred embodiment of the invention.

For instance, as seen in FIG. 3, a preferred embodiment of the device may comprise capacitive array 5 of the invention and further comprise an acoustic signal input such as a microphone input 45, speaker 50 and multiple position toggle switch 55 for the toggling between acoustic and/or non-acoustic input modes.

In this alternative preferred embodiment, acoustic speech signals from microphone 45 are digitized and compared against signal data set 20 and/or with reference data set 35 for a user-defined set of attributes whereby biometric or speech recognition data may be derived utilizing both the acoustic and non-acoustic signals.

Another application of the device is a biometric interface for security purposes on a portable device. That is, the sensor array and circuitry may be used in conjunction with a microphone to lock or unlock the device since non-acoustic, biometric measurements unique to the user may be taken.

Security of the device may be enhanced since one or more parameters specific to the intended user may additionally be encrypted.

Additionally, the disclosure herein contemplates an embodiment embedding the sensor behind the handset's display, conserving limited space on or within a multi-media communication device.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

We claim:

1. A lip reading sensor system comprising:
   a capacitive array comprising a plurality of non-contact proximity-detecting capacitive sensing array pairs having an array output representative of the movement of a user's lips or facial features,
   first electronic circuitry for receiving and processing of the array output into a sequence of signal data sets having a predetermined frame rate,
   a first electronic memory for the receiving and storing of the sequence of signal data sets,
   a second memory for storing at least one reference data set representative of at least one predetermined set of acoustic signals, and,
   second electronic circuitry for comparing at least one of the signal data sets with at least one of the references data sets.

2. The sensor system of claim 1 further comprising an acoustic input.

3. The sensor system of claim 1 wherein the capacitive array comprises a 640×480 array of capacitive sensing array pairs.

4. The sensor system of claim 1 wherein the capacitive array has a surface area of about six cm. by about four cm.

5. The sensor system of claim 1 wherein the first electronic circuitry produces a signal data frame rate of at least ten frames per second.

6. A method for enhancing a speech input in a lip reading device comprising:
   converting the lip or facial movements of a user using a capacitive array comprising a plurality of non-contact proximity-detecting capacitive sensing array pairs into sequences of signal data sets,
   storing at least one of the signal data sets in a first electronic memory,
   providing a reference data set representative of a predetermined set of acoustic signals,
   comparing at least one of the signal data sets with at least one of the reference data sets for the identification of one or more predetermined attributes, and,
   generating an output when one of the predetermined attributes is identified.

* * * * *